United States Patent [19]

Siegl

[11] Patent Number: 4,681,754
[45] Date of Patent: Jul. 21, 1987

[54] COUNTERACTING CYCLOSPORIN ORGAN TOXICITY

[75] Inventor: Helene Siegl, Basel, Switzerland

[73] Assignee: Sandoz Ltd., Basel, Switzerland

[21] Appl. No.: 771,278

[22] Filed: Aug. 30, 1985

[30] Foreign Application Priority Data

Sep. 4, 1984 [GB] United Kingdom ............... 8422253

[51] Int. Cl.⁴ ............... A61K 31/50; A61K 31/495; A61K 37/00

[52] U.S. Cl. .................................. 424/10; 514/11; 514/250

[58] Field of Search .................. 424/10; 514/11, 250

Primary Examiner—Stanley J. Friedman
Attorney, Agent, or Firm—Gerald D. Sharkin; Robert S. Honor; Thomas O. McGovern

[57] ABSTRACT

Improved cyclosporin therapy in particular for counteracting cyclosporin (e.g. Cyclosporine) organ toxicity, comprises adjunct administration of co-dergocrine.

22 Claims, No Drawings

COUNTERACTING CYCLOSPORIN ORGAN TOXICITY

The present invention relates to methods of improving cyclosporin therapy, in particular methods for counteracting cyclosporin nephrotoxicity comprising adjunct administration of co-dergocrine or a pharmaceutically acceptable acid addition salt thereof.

The cyclosporins comprise a class of structurally distinct, cyclic, poly-N-methylated undecapeptides having valuable pharmacological, in particular immunosuppressive, anti-inflammatory and anti-protozoal activity. The first of the cyclosporins to be isolated and the "parent" compound of the class, is the naturally occurring fungal metabolite Cyclosporine, also known as cyclosporin A, the production and properties of which are described e.g. in U.S. Pat. No. 4,117,118. Since the original discovery of Cyclosporine a wide variety of naturally occurring cyclosporins have been isolated and identified and many further non-natural cyclosporins have been prepared by synthetic or semi-synthetic means or by the application of modified culture techniques. The class comprised by the cyclosporins is thus now substantial and includes, for example, the naturally occurring cyclosporins (Thr$^2$)-, (Val$^2$)- and (Nva$^2$)-Cyclosporine (also known as cyclo-sporins C, D and G respectively), as well as various semisynthetic derivatives thereof, such as their dihydro derivatives(e.g. as disclosed in U.S. Pat. Nos. 4,108,985; 4,210,581 and 4,220,641) including e.g. (Dihydro-MeBmt$^1$)-(Val$^2$)-Cyclosporine (also known as dihydrocyclosporin D) and other natural and artificial cyclosporins such as those disclosed in European Patent Publication No. 0,058,134 B1, for example [(D)-Ser$^8$]-Cyclosporine.

[In accordance with now conventional nomenclature for the cyclosporins, these are defined herein by reference to the structure of Cyclosporine (i.e. cyclosporin A). This is done by first indicating those residues in the molecule which differ from those present in Cyclosporine and then applying the term "Cyclosporine" to characterise the remaining residues which are identical to those present in Cyclosporine. Cyclosporine has the formula I

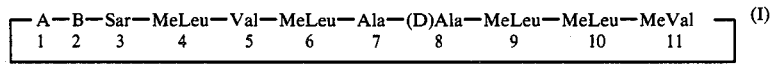

wherein A represents the -MeBmt- [N-methyl-(4R)-4-but-2E-en-1-yl-4-methyl-(L)threonyl] residue of formula II

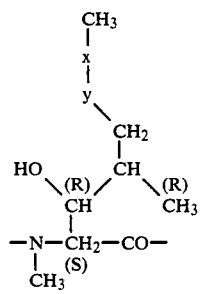

in which —x—y— is —CH=CH— (trans), and B is —α—Abu—. Accordingly (Thr$^2$)-Cyclosporine (cyclosporin C) is the compound of formula I, wherein A has the meaning given above and B is —Thr—, and (Dihydro-MeBmt$^1$)-(Val$^2$)-Cyclosporine (dihydrocyclosporin D) is the compound of formula I, wherein A represents the -dihydro- -MeBmt- residue of formula II above in which —x—y— is —CH$_2$—CH$_2$—, and B is —Val—].

As the "parent" compound of the class, Cyclosporine has so far received the most attention. The primary area of clinical investigation for Cyclosporine has been as an immunosuppressive agent, in particular in relation to its application to recipients of organ transplants, e.g. heart, lung, combined heart-lung, liver, kidney, spleen, bone-marrow, skin and corneal transplants and, in particular, allogenic organ transplants. In this field Cyclosporine has achieved a remarkable success and reputation and is now commercially available and widely employed in clinic.

At the same time, applicability of Cyclosporine to various autoimmune diseases (including for example: multiple sclerosis, Guillan-Barré syndrome, uveitis, myasthenia gravis, Heymann nephritis, juvenile diabetes type I, systemic lupus erythematodes, aplastic anaemia, pure red cell anaemia, idiopathic thrombocytopaenia, polychondritis, sclerodoma, Wegener granulamatosis, dermatomyositis, chronic active hepatitis, autoimmune male infertility, psoriasis and psoriatic arthritis, Steven-Johnson syndrome, idiopathic sprue, Chron's disease, sarcoidosis, glomerulonephritis, interstitial lung fibrosis and primary billiary cirrhosis) and to inflammatory conditions, in particular inflammatory conditions with an aetiology including an autoimmune component such as arthritis and rheumatic diseases, has been intensive and reports and results in vitro, in animal models and in clinical trials are wide-spread in the literature.

A further area of investigation has been potential applicability as an anti-parasitic, in particular anti-protozoal agent, with possible uses suggested including malaria treatment and treatment of schistosomiasis, filariasis, leishmania and coccidiomycosis.

Other cyclosporins exhibit the same overall pharmacological utility as Cyclosporine and various proposals for application, in particular in one or other of the above identified indications, are prevelant in the literature.

Despite the very major contribution which Cyclosporine has made to the art, in particular in the field of transplant surgery and despite its wide acceptance and success in clinic, an obvious negative feature has been its reported organ toxicity, e.g. hepatoxicity and nephrotoxicity. In clinic nephrotoxicity has generally proved of more common concern and while it is evident that in those relatively few cases where a problem arises, nephrotoxicity is dose-related, reversible and not progressive under long term treatment (clinically a problem is only likely to occur in the early phase of Cyclosporine therapy, e.g. immediately subsequent to transplant when differentiation between rejection and nephrotoxicity is difficult) means of reducing this particular side effect and other related side effects of organ toxicity which may occur would clearly be of major benefit. Thus apart from making Cyclosporine therapy more generally acceptable, it would reduce control requirements, e.g. immediately post-transplant, as well as the occasional necessity of employing mixed immunosuppressive therapy (e.g. drug-switching), for example in patients showing especially marked nephrotoxic reactions.

Similarly, while individual cyclosporins other than Cyclosporine may be found to exhibit considerably less toxic, e.g. nephrotoxic, side effects than Cyclosporine or indeed to be generally free of such side reactions, in so far as organ toxicity is or may be a consideration in relation to their clinical application, a means for meeting this problem would equally be of considerable benefit.

In accordance with the present invention it has now surprisingly been found that cyclosporin organ toxicity, e.g. hepatoxic and, in particular, nephrotoxic side effects, induced by cyclosporins, in particular Cyclosporine, can be counteracted by conjugate administration of co-dergocrine or a pharmaceutically acceptable acid addition salt thereof.

Co-dergocrine, which is also known as dihydroergotoxin, is a known commercially available, pharmaceutically active substance which has found widespread application in the treatment of impaired mental function, in particular in the elderly. As a pharmaceutical it is well proven and is notably free from undesirable side effects. Co-dergocrine is thus eminently well suited for use in accordance with the present invention.

Chemically, co-dergocrine is a 1:1:1 mixture by weight of dihydroergocriptin, dihydroergocornin and dihydroergocristin, the dihydroergocryptin component being itself a mixture of the α- and β-isomers in a weight ratio of 2:1 (α:β). Co-dergocrine exists in both free and in acid addition salt form. For pharmaceutical application it is generally employed in pharmaceutically acceptable acid addition salt form, in particular in the form of its methanesulfonate, co-dergocrine methanesulfonate, also known as co-dergocrine mesylate (BAN), dihydroergotoxin methanesulfonate, ergoloid mesylates (USAN) and Hydergin ®. Other pharmaceutically acceptable acid addition salts which may be employed include e.g. the ethanesulfonate, fumarate, maleinate, tartrate and hydrochloride. In general such salt forms have the same or similar level of activity in relation to the present invention as the free compound.

For the sake of convenience, throughout the following description the term "co-dergocrine" is employed to designate both the free form of the compound and its pharmaceutically acceptable acid addition salts, unless otherwise indicated.

In accordance with the foregoing the present invention provides a method of improving cyclosporin therapy which comprises the adjunct administration of co-dergocrine or a pharmaceutically acceptable acid addition salt thereof.

In a more particular embodiment the invention provides a method of counteracting cyclosporin organ toxicity in a subject receiving cyclosporin therapy which comprises the adjunct administration of co-dergocrine or a pharmaceutically acceptable acid addition salt thereof.

The method of the present invention may be employed for example where cyclosporin therapy is applied:

(i) for the purposes of effecting immunosuppression, e.g. to prevent transplant rejection, e.g. following organ or bone marrow transplant, in particular organ transplant of the various types hereinbefore set forth or for the treatment of auto-immune disease, in particular any of the specific autoimmune diseases hereinbefore set forth;

(ii) for the treatment of inflammatory conditions, in particular inflammatory conditions with an aetiology comprising or including an auto-immune component, e.g. for the treatment of arthritis or rheumatic disease; or (iii) for the treatment of parasitic infection, in particular protozoal infection, e.g. for the treatment of any of the parasitic infections hereinbefore set forth, and especially for the treatment of malaria or coccidiomycosis.

In an alternative aspect for the present invention accordingly provides:

A method:

(i) of effecting immunosuppression,
(ii) for the treatment of inflammatory conditions; or
(iii) for the treatment of parasitic infection, in a subject in need of such treatment, which method comprises administering to said subject an effective amount of (a) a cyclosporin and
(b) co-dergocrine or a pharmaceutically acceptable acid addition salt thereof.

The method of the present invention is in particular applicable where the cyclosporin is Cyclosporine. Co-dergocrine is preferably administered in pharmaceutically acceptable acid addition salt form as co-dergocrine mesylate.

As will be appreciated from the preceding description, organ toxicity is not an inevitable corollary of regular cyclosporin therapy and where organ toxicity is observed its degree may vary considerably from subject to subject. In its application to the counteraction of organ toxicity the present invention is accordingly to be understood as providing for the avoidance of organ toxicity where this may otherwise occur as well as its amelioration. The term "counteracting" is accordingly to be understood as connecting both a precautionary or prophylactic as well as curative, or treatmental function.

As previously indicated the method of the present invention is particularly applicable to counteracting of nephrotoxic effect. Kidney damage, e.g. histological change, reduced by administration of co-dergocrine in accordance with the present invention includes: kidney-tubule necrosis or deformation, development of intestitial fibrosis and morphological change or deformation of the small arterys.

Effectiveness of co-dergocrine in reducing cyclosporin organ toxicity, in particular hepatotoxicity and nephrotoxicity, may be demonstrated in animal models and in clinic. A suitable animal trial demonstrating effectiveness is for example carried out employing the SH-rat as test-model, e.g. as follows:

BACK-GROUND

Administration of Cyclosporine to the SH-rat at appropriate dosage rates induces histo-pathological kidney damage and concommitant functional disturbance directly analogous to that observed in man in clinic, as well as histo-pathological damage to the liver and morphological change in the heart. These effects are accompanied by simultaneous stimulation of the RAAS (Renin Angiotensin Aldosterone System), by an increase in blood pressure and heart-frequency, by urea retention and by characteristic change in clinicalchemical serum parameters. The SH-rat accordingly provides an ideal model for determining influence of conjunctly administered drugs on cyclosporin, e.g. Cyclosporine, toxicity, in particular nephrotoxicity.

METHOD

The trial is carried out employing male SH-rats (IVANOVA) weighing ca. 200 g, and with a blood-pressure reading at the commencement of the trial of ca. 150 mm Hg. During the course of the trial the test animals receive standard Nafag 850 feed and water ad libitum.

Three groups each comprising six animals are employed. Group 1 receives 20 mg/kg Cyclosporine dissolved in 10 ml/kg olive oil, per day, p.o. Group 2 receives Cyclosporine treatment as for group 1 plus 0.25 mg/kg co-dergocrine mesylate in 1 ml 5 % glucose/kg, per day, s.c. Group 3, which serves as control, receives 10 ml/kg olive oil, per day, p.o. In group 2 administration of Cyclosporine and co-dergocrine is effected substantially simultaneously.

During the course of the trial water consumption and weight of the test animals is measured daily. Blood-pressure and heart-frequency are measured 2× weekly by indirect plethysmographic recordal via a sphygmomanometer applied to the tail). Blood-pressure/heart frequency measurement for the individual trial groups are recorded 3–4 hours following Cyclosporine treatment. Diuresis analysis is effected 1× per week, on a day between blood-pressure/heart frequency measurement. For this purpose the test animals are loaded with 50 ml/kg 0.9 % NaCl administered orally 3 hours following Cyclosporine/placebo, with subsequent urine collection over 3 hours from individual rats. In the 2nd, 3rd and 4th week of the trial, 0.8 ml blood samples are collected 5 hours subsequent to Cyclosporine/placebo administration via retro-orbital eye puncture. In the 3rd week of the trial a further 0.8 ml blood sample is collected for PRA (Plasma Renin Activity) determination. The trial continues for 28 days at the end of which surviving animals are sacrificed. The kidneys as well as the liver and hearts of all animals including those dying during the course of the trial are collected and subjected to histological examination.

The following recorded data are evaluated:
(1) Kidney, liver and heart histology. (Occurrence of kidney tubule vacuolisation and irregularity and signs of arterial pathology; occurrence of liver swelling and necrosis; occurrence of heart tissue fibrosis and necrosis).
(2) Body weight.
(3) Water consumption.
(4) Blood-pressure and heart frequency.
(5) Urine volume and $Na^+$ and $K^+$ excretion.
(6) PRA.
(7) Blood serum parameters: BUN (Total nitrogen content), creatinine and $Ca^{2+}$.

RESULTS

Rats in group 1 exhibit symptoms of Cyclosporine induced organ damage, in particular of nephrotoxic reaction, and of concomitant functional disturbance as compared with rats in control group 3.

Histopathological changes found in comparison with the control group include: histopathological change in the kidney tubuli and in the renal arterial net; liver necrosis and symptoms of liver blockage; myocardial fibrosis; light myonecrosis. Concommitant functional disturbance observed in comparison with the control group includes: reduction of body weight; slight initial increase in water consumption followed by subsequent reduction during the course of the trial; significant increase in blood pressure, heart frequency and PRA; a slight tendency to urine retention and an increase in $Na^+$ and $K^+$ quotient; increase in BUN without significant change in respect of creatinine. Only 1 out of 6 rats in group 1 survives to the end of the trial compared with 6 out of 6 rats in control group 3.

Symptoms of Cyclosporine induced organ damage, in particular of nephrotoxic reaction, and concomitant functional disturbance are markedly reduced in rats in group 2 (receiving Cyclosporine+co-dergocrine mesylate) as compared with rats in group 1, and results recorded closely parallel those recorded for control group 3. In particular all histopathological changes found in group 1 (kidney, liver and heart) are found to be greatly reduced).

In comparison with group 1, loss of body weight is reduced; water consumption is significantly increased; blood-pressure, heart frequency and PRA are reduced to the level of control group 3; light salidiuresis is observed. In group 3, 6 out of 6 rats survive until the end of the trial.

Effectiveness of co-dergocrine in reducing cyclosporin, e.g. Cyclosporine, organ toxicity may also be demonstrated in clinical trials, e.g. performed as follows:

CLINICAL TRIAL

Subjects are divided into two groups, mixed ♂ and ♀, all aged under 65 years of age. In both groups only those having had at least 2 units of blood before or at the time of surgery are transplanted. The following exclusion criteria are applied: Kidney from a related donor; third or subsequent transplant; insulin dependent diabetes mellitus; ♀ of childbearing age not using an effective medically approved method of birth control; acute or chronic liver disease; patients taking other immunosuppressive medication; patients who have within 3 months prior to admission received any drug which has caused toxicity to a major system; history of malignancy; patients who are Australia antigen positive. Kidneys are taken from donors with a negative crossmatch, HLA A, B and DR. Patients entering the study are randomly allocated to Group 1, receiving Cyclosporine+low-dose steroid therapy (control group) or Group 2, receiving Cyclosporine+low-dose steroid+co-dergocrine mesylate (test group). The following treatment plan is employed:

1. Intraoperative protocol (both groups)

During kidney implantation 250 mg frusemide, repeated in 2 hours if urine flow <80 ml/hour, 100 ml, 20 % mannitol and 500 mg methylprednisolone administered i.v.

2. Control group

Receives regular Cyclosporine+low-dose prednisone therapy as described by Thiel et al, Klin. Wochenschr. 61, 991–1000 (1983) with Cyclosporine administered i.v. for the first 2–3 days post-transplant and subsequently p.o., plus a placebo substitute for co-dergocrine mesylate. Cyclosporine dosage reduction is effected in accordance with trough blood levels as measured by RIA. After the first week post transplant the desired trough blood level is ca. 300–800 ng/ml. Blood samples are drawn in the morning before the morning Cyclosporine dose.

3. Test group

Received regular Cyclosporine+low-dose prednisone therapy as for the control group plus co-dergocrine mesylate. The co-dergocrine mesylate is administered to each subject (i) for the first 10 days post-transplant at a daily dose of 1.5 mg by infusion over 2 hrs. and (ii) subsequently at a daily dose of 4, 6, 8, 9 or 12 mg administered in two equally divided doses 1× in the morning and 1× in the evening. Treatment with co-dergocrine mesylate continues for 12 months.

The following laboratory investigations are conducted at 1, 3, 6, 9 and 12 months post-transplant:
Urine (24 hour values)—Volume, protein excretion and creatinine clearance
Blood chemistry—$Na^+$, $K^+$, bicarbonate, glucose, creatinine, urea, bilirubin (total), protein (total), albumin, alkaline phosphatase, SGOT, SGPT, GGT ($\gamma$-glutamyl transferase), $Ca^{++}$, phosphate and uric acid.
The following evaluation parameters are applied:
patient survival,
kidney survival and function,
specific side effects, including osteoporosis, secondary hyperparathyrodism, metabolic disturbance, hypertrichosis, cataracts, aseptic bone necrosis,
amount of steroids used,
number of rejection crises.

Results obtained indicate equivalence of immunosuppressive therapy for groups 1 and 2, e.g. as evidenced by patient/kidney transplant survival rate and relative occurrence of rejection crisis. Subjects in group 2 receiving co-dergocrine mesylate however show significant improvement in respect of parameters indicative of nephrotoxic side effect or other renal dysfunction, as compared with subjects in group 1 receiving co-dergocrine mesylate placebo only.

In accordance with the present invention it has further and most importantly been found that, though adjunct administration of co-dergocrine reduces cyclosporin, e.g. Cyclosporine, organ toxicity, e.g. nephrotoxicity, other pharmacological activity, e.g. immunosuppressive, anti-inflammatory or anti-protozoal activity, of administered cyclosporin remains uninfluenced. The absence of any influence on e.g. the immunosuppressive and anti-inflammatory activity of administered cyclosporin, e.g. Cyclosporine, may be demonstrated in standard animal tests, e.g. as described below, and in clinic.

TEST 1: IMMUNO-SUPPRESSIVE ACTIVITY: LOCAL GRAFT-VERSUS-HOST (GVH) REACTION IN THE RAT

The test is carried out employing rats (F344×WF)FI sensibilized by injection into the hind-foot of spleen cells taken from ♀ Wistar-Furth (WF) rats. The test animals are divided into groups of 8. One series of groups receives Cyclosporine at dosages of 36 and 25 mg/kg p.o. on 4 successive days starting on the day of sensibilisation. A second series receives co-dergocrine mesylate administered at dosages of 0.25 mg/kg i.v. on 4 successive days starting on the day of sensibilisation. A third series receives Cyclosporine +co-dergocrine mesylate administered at dosages of 36 or 25 mg/kg p.o. (Cyclosporine) and 0.25 mg/kg i.v. (co-dergocrine mesylate) concommittantly on 4 successive days starting on the day of sensibilization. GVH reaction is determined by measurement of increase in lymphe node weight compared with untreated controls.

Results obtained in the above test in rats receiving Cyclosporine alone and in rats receiving Cyclosporine plus co-dergocrine mesylate indicate an $ED_{50}$ for Cyclosporine of 27 mg/kg in both instances, demonstrating that the co-dergocrine mesylate has no influence on Cyclosporine activity. Results obtained on administration of co-dergocrine mesylate alone indicate that this has no significant effect as compared with untreated controls.

TEST 2: IMMUNO-SUPPRESSIVE ACTIVITY: ANTI-BODY PRODUCING CELL DEVELOPMENT IN THE MOUSE (PFC TEST)

The test is carried out employing ♀ OFI mice sensibilized by i.v. administration of ca. $1\times10^8$ sheep erythrocytes (SRBC). The test animals are divided into groups of 5.

One series of groups receives Cyclosporine administered at dosages of 50 and 70 mg/kg p.o. on 3 successive days starting on the day of sensibilization. A second series receives co-dergocrine mesylate administered at dosages of 0.25, 2.5 or 25 mg/kg i.v. on 3 successive days starting on the day of sensibilization. A third series receives Cyclosporine +co-dergocrine mesylate administered at dosages of 50 or 75 mg/kg p.o. (Cyclosporine) and 0.25 mg/kg i.v. (co-dergocrine mesylate) concommitantly on 3 successive days starting on the day of administration.

The spleens are removed on day 4 and a cell suspension prepared and incubated with fresh SRBC antigen on soft agar. After addition of compliment, which, together with anti-body secreted from the sensibilized cells, dissolves SRBC in the vicinity of secreting cells, plaque development is counted and compared with results obtained employing untreated control mice.

Results obtained in the above test (i) in mice receiving Cyclosporine alone and (ii) in mice receiving Cyclosporine plus co-dergocrine mesylate indicate an $ED_{50}$ for Cyclosporine of (i) 40 and (ii) 55 mg/kg respectively, demonstrating absence of any significant influence of co-dergocrine mesylate on Cyclosporine activity. Results obtained on administration of co-dergocrine mesylate alone, indicate that this has no significant effect as compared with untreated controls.

TEST 3: ANTI-INFLAMMATORY ACTIVITY: ADJUVANT ARTHRITIS THE RAT

For this test adjuvant arthritis is induced in accordance with the method described by Pearson and Wood, "Arthr. Rheum." 2, 440 (1959). OFA ♀ rats are employed as test animals. The rats are divided into groups receiving: (a) 3 or 10 mg/kg Cyclosporine p.o./day: (b) 0.25 mg/kg co-dergocrine mesylate s.c./day: (c) 3 or 10 mg/kg Cyclosporine p.o./day plus 0.25 mg/kg co-dergocrine mesylate s.c./day. Administration is effected in all cases on successive days for 14 days starting on day 1 after antigen administration and inflammatory reaction is determined on day 19 after antigen administration.

Results obtained (i) in mice receiving Cyclosporine alone and (ii) in mice receiving Cyclosporine plus co-dergocrine mesylate indicate an $ED_{50}$ for Cyclosporine of (i) 4.2 and (ii) 4.5 mg/kg respectively, demonstrating the absence of any significant influence of co-dergocrine mesylate on Cyclosporine activity. Results obtained on administration of co-dergocrine mesylate alone, indicate that this has no significant effect as compared with untreated controls.

In accordance with the method of the present invention, cyclosporin and co-dergocrine may be administered separately at different times during the course of therapy or substantially concommitantly. Thus treatment with co-dergocrine may commence prior to cyclosporin treatment, or subsequent to commencement of cyclosporin treatment. The present invention is to be understood as embracing all such regimes of treatment and the term "adjunct administration" is to be interpreted accordingly. In practicing the method of the invention commencement of co-dergocrine administration prior to cyclosporin treatment may in some instances and depending on e.g. the purpose of cyclosporin therapy and the condition of the subject to be treated, be especially advantageous. Thus commencement of treatment with co-dergocrine up to 7 days or more in advance of cyclosporin treatment may provide an additional and beneficial pre-protective effect against cyclosporin, e.g. Cyclosporine, organ toxicity, e.g. nephrotoxicity. Moreover in accordance with the present invention it has further been found that, in addition to reducing cyclosporin organ toxicity, co-dergocrine may also potentiate the immunosuppressive effectiveness of cyclosporins, e.g. of Cyclosporine, for example when used in relation to transplant surgery, and for this purpose administration of co-dergocrine in advance of cyclosporin therapy may in particular be indicated. Thus results obtained in accordance with the method of TEST 1 above, with administration of co-dergocrine mesylate at the indicated dosages, but beginning 7 days prior to, rather than concommitantly with, administration of Cyclosporine, indicate that the immunosuppressive activity of Cyclosporine in this test is potentiated.

Doses of cyclosporin to be administered in practicing the method of the present invention will of course vary depending upon, e.g. the particular cyclosporin employed, the mode of administration, the condition to be treated (e.g. whether treatment is for the purposes of immunosuppression or otherwise, and if for immunosuppression whether for use in relation to e.g. organ transplant, bone-marrow transplant, or the treatment of autoimmune disease), as well as the effect desired. In addition, dosaging will generally require adjustment for individual patients in order to establish an appropriate long-term drug serum concentration, e.g. by administration of an initial daily starting or "loading" dose with subsequent dose adjustment (generally dose reduction) in accordance with serum levels, e.g. as determined by regular RIA monitoring.

In general amounts administered will be of the same or similar order to those conventionally employed in cyclosporin therapy, e.g. Cyclosporine therapy, i.e. required to achieve (i) immunosuppressive, (ii) anti-inflammatory, or (iii) anti-parasitic effectiveness. Thus in general satisfactory results are obtained on administration in a dose range of from about 1 or about 5 to about 50 mg/kg/day (e.g., in the case of Cyclosporine, from about 5 or about 10 to about 20 mg/kg/day during the initial phase of therapy, reducing to a maintainance dose of from about 1 or about 5 to about 10 mg/kg/day) administered to the patient orally, once or in divided doses 2 or 3× a day. Where i.v. administration is required, e.g. administration by infusion (for example in the initial phase of treatment) lower dosages, e.g. of the order of from about 0.5 or about 1 to about 10 (e.g. in the case of Cyclosporine, from about 1 or about 3 to about 5 mg/kg/day for an initiating dose, or to about 2.5 mg/kg/day for a maintainance dose) are generally indicated, with lower dose ranges being indicated where cyclosporin activity is potentiated by conjuntly administered co-dergocrine, e.g. in preventing transplant rejection.

Doses of co-dergocrine to be administered in practicing the method of the present invention, e.g. for achieving effectiveness in counteracting cyclosporin induced organ toxicity, will also vary, e.g. depending on the mode of administration, the cyclosporin therapy applied (e.g. whether immunosuppressive or otherwise/cyclosporin dosaging required) and the particular cyclosporin employed.

Administration may be enteral (e.g. oral) or parenteral, (e.g. i.v.). A suitable daily parenteral dosage for use in accordance with the invention being from about 0.1 to about 10.0, e.g. from about 1.0 to about 7.5, in particular from about 1.5 to about 6.0 mg administered once, e.g. by i.v. drip or slow i.v. injection, or i.m. or s.c. 1 to 3× daily. Suitable unit dosage forms for i.v. administration in accordance with the invention accordingly comprise from about 0.03 to about 10.0, e.g. from about 0.3 to about 7.5, in particular from about 0.5 to about 6.0 mg of co-dergocrine, e.g. of co-dergocrine mesylate/unit dosage e.g. /ampoule.

Where oral administration is contemplated suitable daily dosages are of the order of from about 1 to about 15 mg, e.g. from about 1 to about 10 mg, in particular from about 4.5, 6 or 9 mg/day administered once or in divided dosages 2 to 4× daily. Suitable unit dosage forms for oral administration in accordance with the invention accordingly comprise from about 0.25 to 15, e.g. from about 0.25 to about 10 mg.

By oral and parenteral dosage forms for cyclosporins, e.g. Cyclosporine, and co-dergocrine, e.g. of co-dergocrine mesylate, suitable, for use in practicing the method of the present invention are known in the art and are commercially available.

I claim:

1. A method of counteracting cyclosporin organ toxicity in a subject in need of such treatment which comprises adjunctly administering co-dergocrine or a pharmaceutically acceptable acid addition salt thereof to the subject in an amount effective to counteract cyclosporin organ toxicity.

2. A method according to claim 1 of prophylactically counteracting cyclosporin organ toxicity.

3. A method according to claim 1 of treating cyclosporin organ toxicity.

4. A method according to claim 1 of counteracting cyclosporin organ toxicity in a subject administered an immunosuppressant effective amount of a cyclosporin.

5. A method according to claim 1 of counteracting cyclosporin organ toxicity in a subject administered an anti-inflammatory effective amount of a cyclosporin.

6. A method according to claim 1 of counteracting cyclosporin organ toxicity in a subject administered an anti-parasitic effective amount of a cyclosporin.

7. A method according to claim 1 in which co-dergocrine is adjunctly administered as co-dergocrine mesylate.

8. A method according to claim 1, in which from about 0.1 to about 10 mg of co-dergocrine or a pharmaceutically acceptable acid addition salt thereof is administered i.v. daily.

9. A method according to claim 1 in which from about 1.0 to about 7.5 mg of co-dergocrine is adjunctly administered i.v. daily.

10. A method according to claim 1 in which from about 1.5 to about 6.0 mg of co-dergocrine is adjunctly administered i.v. daily.

11. A method according to claim 1 in which from about 0.03 to about 10 mg of co-dergocrine or a pharmaceutically acceptable acid addition salt thereof in unit dose form is administered i.v.

12. A method according to claim 1 in which from about 0.3 to about 7.5 mg of co-dergocrine or a pharmaceutically acceptable acid addition salt thereof in unit dose form is administered i.v.

13. A method according to claim 1 in which from about 0.5 to about 6.0 mg of co-dergocrine or a pharmaceutically acceptable acid addition salt thereof in unit dose form is administered i.v.

14. A method according to claim 1, in which from about 1 to about 15 mg of co-dergocrine or a pharmaceutically acceptable acid addition salt thereof is orally administered daily.

15. A method according to claim 1, in which from about 1 to 10 mg of co-dergocrine or a pharmaceutically acceptable acid addition salt thereof is orally administered daily.

16. A method according to claim 1 in which about from 4.5, 6 or 9 mg of co-dergocrine or a pharmaceutically acceptable acid addition salt thereof is orally administered daily.

17. A method according to claim 1, in which from about 0.25 to about 15 mg of co-dergocrine or a pharmaceutically acceptable acid addition salt thereof in unit dose form is orally administered.

18. A method according to claim 1, in which from about 0.25 to about 10 mg of co-dergocrine or a pharmaceutically acceptable acid addition salt thereof in unit dose form is orally administered.

19. A method according to claim 1, in which 1.5 mg of co-dergocrine or a pharmaceutically acceptable acid addition salt thereof is administered daily by infusion.

20. A method according to claim 1, in which administration of co-dergocrine is begun up to 7 days or more prior to the administration of the cyclosporin.

21. A method according to claim 4, in which the administration of co-dergocrine is begun 7 days prior to the administration of cyclosporin.

22. A method according to claim 1 wherein the cyclosporin is Cyclosporine.

* * * * *